US008563050B2

(12) United States Patent
Hidvégi

(10) Patent No.: US 8,563,050 B2
(45) Date of Patent: Oct. 22, 2013

(54) PHARMACEUTICAL COMPOSITION CONTAINING A FERMENTED, DEHYDRATED MATERIAL WITH AMORPHOUS CRYSTALLINE STRUCTURE

(75) Inventor: Máté Hidvégi, Budapest (HU)

(73) Assignees: Máté Hidvégi, Budapest (HU); BIROPHARMA Elso Magyar Biotechnologiai Kft., Kunfeherto (HU); TAPSZER Elelmiszeripari Gyarto és Kereskedelmi Kft., Budapest (HU)

( * ) Notice: Subject to any disclaimer, the term of this patent is extended or adjusted under 35 U.S.C. 154(b) by 0 days.

(21) Appl. No.: 13/254,632

(22) PCT Filed: Mar. 3, 2010

(86) PCT No.: PCT/HU2010/000025
§ 371 (c)(1),
(2), (4) Date: Sep. 2, 2011

(87) PCT Pub. No.: WO2010/100514
PCT Pub. Date: Sep. 10, 2010

(65) Prior Publication Data
US 2012/0003302 A1 Jan. 5, 2012

Related U.S. Application Data

(60) Provisional application No. 61/209,200, filed on Mar. 3, 2009.

(30) Foreign Application Priority Data

Sep. 29, 2009 (HU) ...................................... 0900614

(51) Int. Cl.
A61K 36/00 (2006.01)
A61K 9/00 (2006.01)
A61K 9/127 (2006.01)
A61K 9/28 (2006.01)

(52) U.S. Cl.
USPC ............ 424/725; 424/400; 424/474; 424/450

(58) Field of Classification Search
None
See application file for complete search history.

(56) References Cited

U.S. PATENT DOCUMENTS

2005/0281898 A1 12/2005 Sugiyama et al.

FOREIGN PATENT DOCUMENTS

| HU | 9802048 A2 * | 8/2000 |
| JP | 8-337536 A | 12/1996 |
| WO | WO 99/08694 A1 | 2/1999 |
| WO | WO 0130351 A1 * | 5/2001 |
| WO | WO 2004/014406 A1 | 2/2004 |

OTHER PUBLICATIONS

Cosgrove et al, Isolation of Methoxy- and 2;6-dimethoxy-p-benzoquinone from fermented wheat germ, Nature, 169: 966-967, 1952.*
"Risk factor for cancer" from Merck Manual, pp. 1-4, accessed on Apr. 14, 2009.*
"Introduction to Cancer" from Merck Manual, pp. 1, accessed on Mar. 5, 2008.*
Tomatis, Environmental cancer risk factors, Acta oncologica (Stockholm, Sweden), (1988) vol. 27, No. 5, pp. 465-472.*
Kronborg, Population screening for colorectal cancer, the goals and means, Annals of medicine, (Oct. 1991) vol. 23, No. 4, pp. 373-379.*
Garewal et al, Clinical experience with the micronucleus assay, Journal of Cellular Biochemistry, (1993) vol. 52, No. Suppl. 17 F, pp. 206-212.*
Cheng et al, A novel approach to microcalcification detection using fuzzy logic technique, IEEE transactions on medical imaging, (Jun. 1998) vol. 17, No. 3, pp. 442-450.*
Granziero et al. Adoptive immunotherapy prevents prostate cancer in a transgenic animal model, Eur. J. Immunol. 1999, 29:1127-1138.*
Byers, T, What can randomized controlled trials tellus about nutrition and cancer prevention, CA Journal, vol. 49, No. 6, Nov./Dec. 1999.*
Jayaraman et al, In-vitro antimicrobial and antitumor activities of Stevia rebaudiana (Asteraceae) leaf extracts. Tropical Journal of Pharmaceutical Research (2008) vol. 7, No. 4, pp. 1143-1149.*
International Search Report, dated Aug. 27, 2010, issued in PCT/HU2010/000025.

* cited by examiner

Primary Examiner — Qiuwen Mi
(74) Attorney, Agent, or Firm — Birch, Stewart, Kolasch & Birch, LLP

(57) ABSTRACT

The invention concerns a high water soluble product, containing a dehydrated material, obtained by fermenting wheat germ in aqueous medium in the presence of microorganisms of the Saccharomyces genus, forming amorphous crystal structure with inert auxiliary materials), commonly used in preparation of drugs. The invention also relates to the production process of said products, to immunostimulatory, immunomodulatory, antitumor and cardiovaskular pharmaceutical preparations containing them, and to the therapeutic methods for their use.

11 Claims, 3 Drawing Sheets

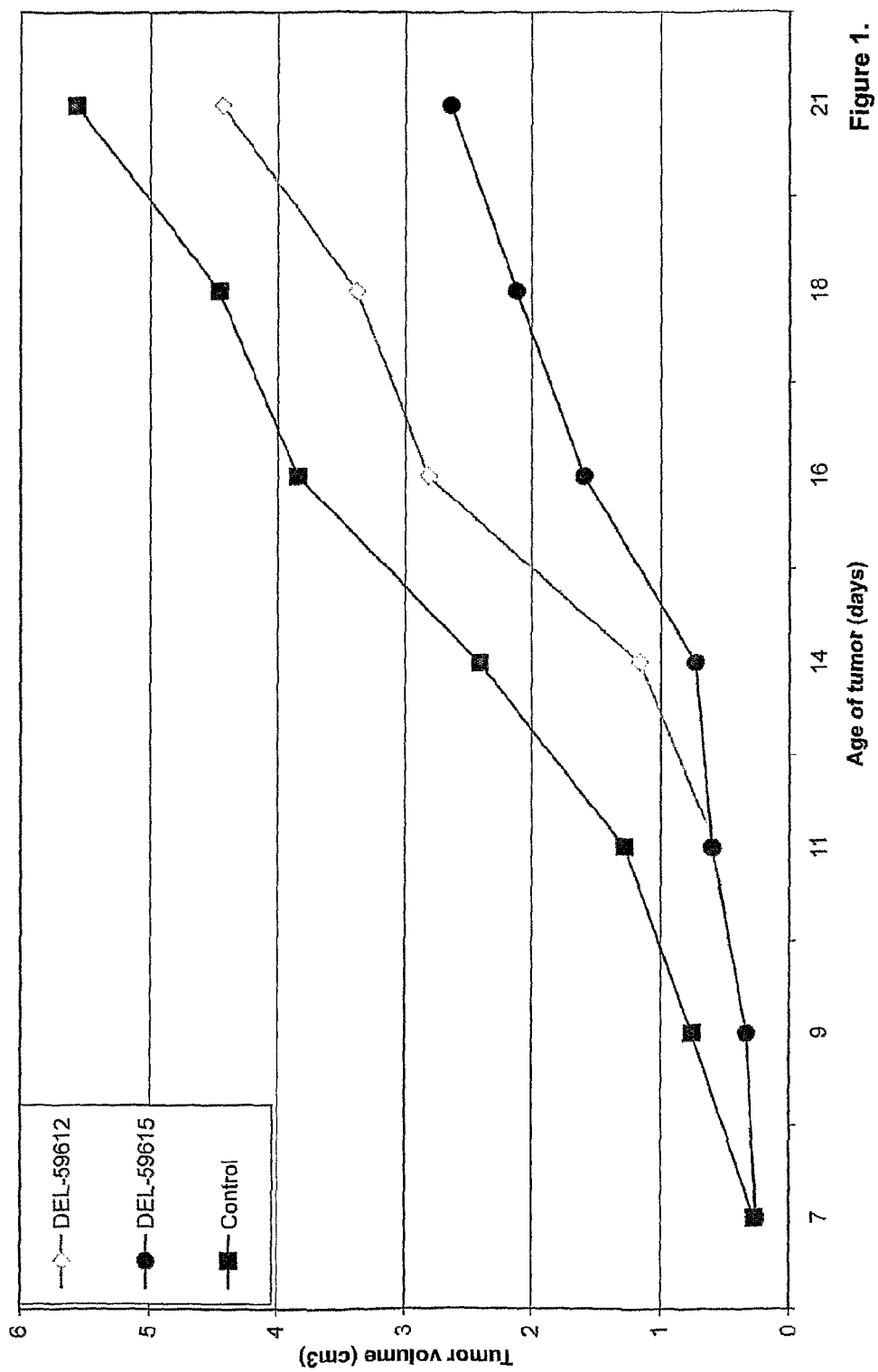

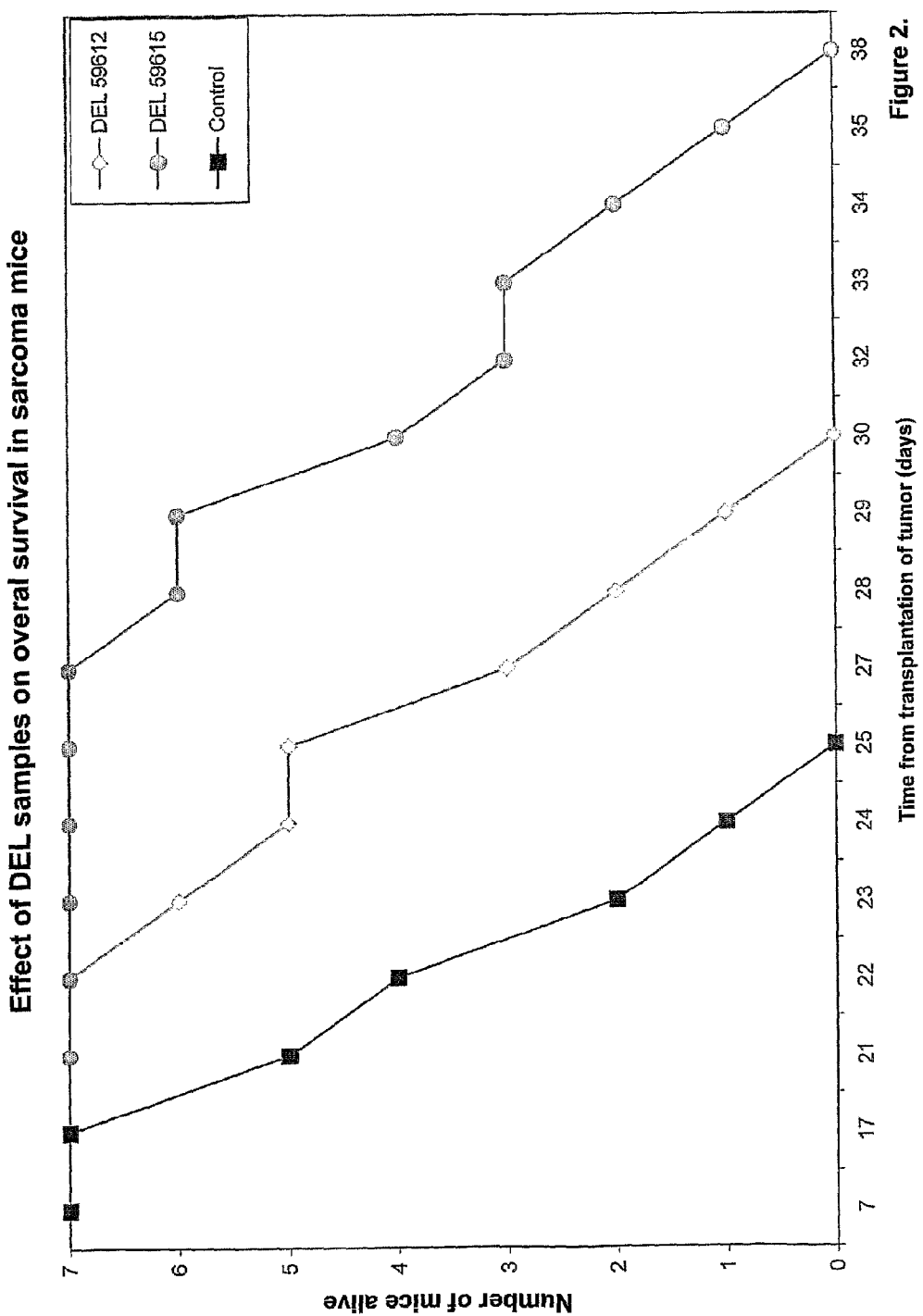

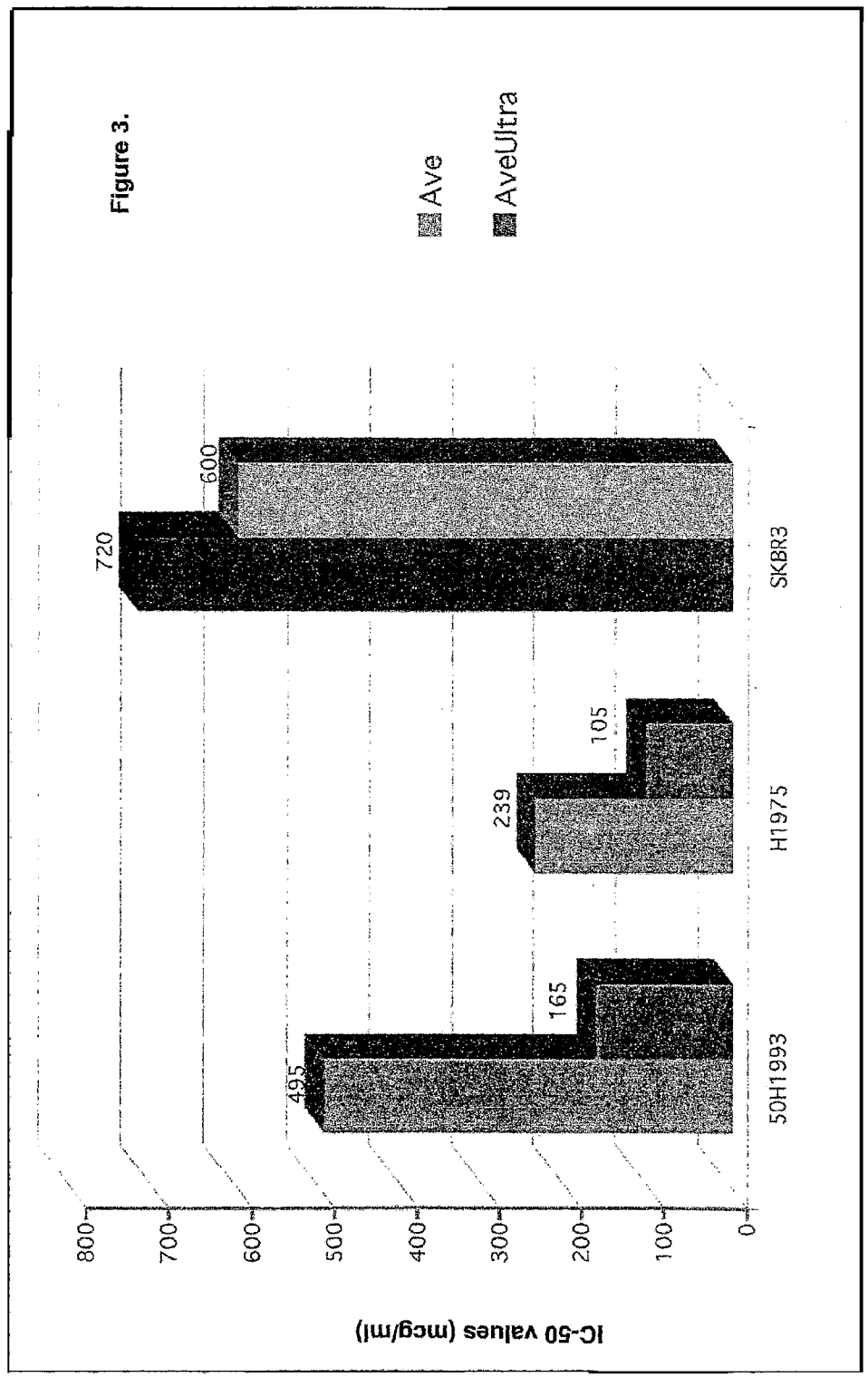

PHARMACEUTICAL COMPOSITION CONTAINING A FERMENTED, DEHYDRATED MATERIAL WITH AMORPHOUS CRYSTALLINE STRUCTURE

CROSS REFERENCE TO RELATED APPLICATIONS

This application is the National Phase of PCT/HU2010/000025 filed on Mar. 3, 2010, which claims priority under 35 U.S.C. 119(e) to U.S. Provisional Application No. 61/209,200 filed on Mar. 3, 2009 and under 35 U.S.C. 119(a) to Patent Application No. P0900614 filed in Hungary on Sep. 29, 2009, all of which are hereby expressly incorporated by reference into the present application.

The subject of the invention is a product, containing dehydrated fermented material of high water solubility and having amorphous crystal structure, and the process for its preparation.

It is known that the dried material (active ingredient) obtained by fermenting wheat germ in aqueous medium in the presence of *Saccharomyces cerevisiae*, and by drying the fermentation liquid, has immunostimulatory and metastasis inhibiting (Hungarian Patent No. 223 344) and anti-arthritis (EP 1536809 A1) effects. The dried material is not a single compound, but a material mixture (Hungarian Patent No. 223 344). It is marketed under the names Avemar®, Avé® (in the following: previous product). Human clinical studies proved that the fermented wheat germ extract is effective in the treatment of e.g. skin melanoma (Cancer Biother Radiopharm. 2008 Aug; 23(4): 477-82), rheumatoid arthritis (Clip Exp Rheumatol. 2006 M Jun; 24(3): 325-8), colorectal cancer (Br J Cancer 2003 Aug 4; 89(3)(465-9).

Drawbacks of the use of the previous product are due to the following factors: it contains 15-20 % (w/w) maltodextrine—because the thermoplastic material obtained by concentrating the fermentation liquid is dried by spray-drying—, it also contains 40-45% sweetener—because of organoleptic reasons—thus, the weight of a single dose of the product is large. The instant properties of the product are also poor. It has unpleasant smell and taste which hinder its widespread use.

We set the target to develop such a product from wheat germ ferment which preserves or exceeds the efficacy of the previous product, does not contain maltodextrine, can be easily dissolved in water and possesses pleasant organoleptic properties.

Dehydration can be carried out by different ways, such as spray-drying, lyophilization fluid drying, or by other vacuum drying techniques, in the case of dietary supplemer spray-drying is widely used.

We found that, by the use of the dehydrating technique according to the present invention, a new product can be manufactured which has improved solubility, better taste and higher efficacy than the previous one.

Surprisingly, we found that if 0,1-5% (w/w) taste improving material (s) and if desired surfactant(s) and other auxiliary materials, commonly used in pharmaceutical technology, dissolved in water or in water-miscible solvent, are added preferably to the concentrated and cooled fermentation liquid, and subsequently, the concentrate is lyophilized, a new product with improved characteristics can be obtained.

Such inert auxiliary materials can be taste-improving materials which can mask the unpleasant taste and/ or smell of extracts, especially of plant origin, and if desired surfactants and optionally other auxiliary materials used at pharmaceutical make up/formulat log/manufacturing.

As surfactants, known surface-stabilizing, dispersing, emulsifying agents can be used. The particle size of the product according to the invention can be influenced by the applied surface-stabilizing, dispersing and emulsifying agent, respectively. Preferably, a product is manufactured with micro-, and nano-particle size distribution, respectively. The particle size is preferably between 100 micrometer and 50nanometer.

Investigated by X-ray diffraction measurement, the products, according to the invention, have amorphous structure.

According to the above, the subject of our invention comprises a new high water soluble, amorphous dehydrated product, obtained by fermenting wheat germ in aqueous medium in the presence of microorganisms of the *Saccharomyces* genus, forming and lyophilizing in the presence of 0.1-5% (w/w) taste improving material, 0-20% (w/w) surfactant, and 0-60% (w/w) other auxiliary materials commonly used in drug manufacturing.

Particularly, the subject of our invention comprises a new high water soluble, amorphous dehydrated product, obtained by fermenting wheat germ in aqueous medium in the presence of microorganisms of the *Saccharomyces* genus, and by mixing the preferably concentrated and cooled fermentation liquid thus obtained with 0.1-5% (w/w) taste improving material, 0-20% surfactant, and 0-60% (w/w) other auxiliary materials commonly used in drug manufacturing, and by lyophilizing of the mixture thus obtained.

The concentration of the inert auxiliary material in the product can greatly vary. The new product is easily dissolving in water.

The subject of our invention also comprises a process for the preparation of the new high water soluble, amorphous dehydrated product, characterized by fermenting wheat germ in aqueous medium in the presence of microorganisms of the *Saccharomyces* genus, and 1. a.) concentrating and cooling the thus resulted fermentation liquid, adding to it 0.1-5% (w/w) taste improving material, 0-20% (w/w) surfactant, and 0-60% (w/w) other auxiliary materials commonly used in drug manufacturing dissolved in water, and lyophilizing the mixture thus obtained, or
b.) cooling the thus resulted fermentation liquid, adding to it f 0.1-5% (w/w) taste improving material, 0-20% (w/w) surfactant, and 0-60% (w/w) other auxiliary materials commonly us in drug manufacturing, dissolved in water, and concentrating and lyophilizing the mixture thus obtained.

For microorganisms belonging to the *Saccharomyces* genus, *Saccharomyces cerevisiae, Saccharomyces bayanus* and *Saccharomyces boulardii* can be used, but other microorganisms used in the fermentation of foods can also be applied. Preferably, the fermentation is carried out by using *Saccharomyces cerevisiae*.

As surfactants, among others, polyoxyethylene alkyl ethers; polyoxyethylene sorbitane fatty acid esters; polyethylene glycols; sodium dodecyl sulfate; sodium lauryl sulfate; cellulose derivatives; polyvinylpyrrolidone; block copolymers of ethylene oxide and propylene oxide; acrylic acid polymers; phosphatides, such as lecithin; phospholipids; chitosan, and other surfactants being known from the literature can be used.

As taste improving/ flavouring agents, among others, natural and artificial sweeteners, such as stevia (Stevia rebaudiana extracts), magnasweet (mono ammonium glycyrrhizinate); flavouring compounds, such as different fruit extracts and/or menthol, sweet fennel oil; citric oil can be used.

If desired, other auxiliary materials, approved for pharmaceutical applications, can also be added to the solid pharmaceutical preparations according to the invention, such as filling-, thinning- and binding materials, like lactose, glucose, mannitol, saccharose, silicic acid, various starches, microcrystalline cellulose, polyvinylpyrrolidone; polyethylene glycols; polyoxyethylene; sugar alcohols; saccharides; hydroxypropyl methyl cellulose, hydroxypropyl cellulose, methyl cellulose, alginates, gelatine, dicalcium phosphate; adsorbent materials, like colloide silicon dioxide; lubricants, like Aerosil®, talcum, magnesium stearate, calcium stearate, stearic acid, silica gel, calcium hydrogen phosphate, sodium lauryl sulfate; desintegrans, like calcium carbonate, starch, celluloses, polymethacrylates, alginates; materials delaying release dissolution, like liphophylic materials, e.g. paraffin saccharose, hydroxylpropyl cellulose, lubricants, e.g. magnesium stearate, calcium stearate, polyethylene glycols, fumaric acid, adipinic acid; preservatives, like sodium sorbate, methylparabenzoate, film-forming materials, like hydroxypropyl methyl cellulose, polyethylene glycols, titanium dioxyde, etc.

The liquid pharmaceutical forms may contain inert solvents, like water, ethanol, polyols, glycerin; moisturizing-, emulsifying and dispersing agents, like polyoxyethylene alkyl ethers; polyoxyethylene sorbitane fatty acid esters; polyethylene glycols; sodium dodecyl sulfate; sodium lauryl sulfate; cellulose derivatives; polyvinylpyrrolidone; block copolymers of ethylene oxide and propylene oxide; acrylic acid polymers; phosphatides, such as lecithin; phospholipids; chitosan; isotonic agents, like sugars, sodium chloride.

The above mentioned auxiliary materials are well known for professionals.

The subject of our invention further comprises pharmaceutical preparations containing as active ingredient the new product according to the invention, which contains dehydrated fermented material, forming amorphous crystal structure with inert auxiliary material(s), usually applied in the preparation of drugs.

The pharmaceutical preparations according to the invention can be applied in solid or liquid dosage forms, including lyophilized form, controlled release form, delayed release form, extended release form, etc.

The pharmaceutical preparations according to the invention can preferably be formulated as tablet, coated tablet, extended release tablet, dragée, granule, sachet, capsule, solution, suspension, emulsion, spray, suppository, ointment, patch, liposome with the application of auxiliary materials and procedures commonly used in pharmaceutical technology.

The pharmaceutical preparations according to the invention can be manufactured by the procedures commonly used in drug manufacturing, however, we can perform the procedure in such a way that for instance the auxiliary materials of tabletting are added to the concentrated fermentation liquid (concentrate) and the thus resulted mixture is dehydrated. By this way for instance granulation, usually done before tabletting, can be omitted. After choosing the appropriate auxiliary materials, the granulates, according to the invention, can be manufactured by both dry- and wet granulation.

The subject of our invention further comprises the application of the product, according to the invention, for the manufacturing of pharmaceutical preparations with immunomodulatory and antitumor properties, and for production of dietary supplement, medical food or dietary food for special medical purpose for mammals, respectively.

For the treatment and/or prevention of cancer, and/or for modulating pathological immune functions, and/or for preventing the development of infectious diseases by strengthening the immune defense mechanisms, the effective amount of the pharmaceutical preparation of the invention is given to sick or healthy people.

The subject of our invention further comprises the application of the product, according to the invention, for the treatment of cardiovascular and metabolic symptoms.

The effective dosage may vary according to the type of disease, the state, age, body weight of the patient. The single daily dosage for a 70 kg weight human being is usually 1-10 g active ingredient.

Further particulars of the invention are described in the examples, without limiting the invention to the examples.

EXAMPLE 1

111 kg of *Saccharomyces cerevisiae* is suspended in 3550 liters of water of 30° C., and 333 kg of wheat germ is added to it, and the suspension is aerated and mixed for 18 hours. The fermentation liquid is then separated and filtered to cell-free and concentrated in vacuum. The dry matter content of the concentrate is 17% (w/w). 0.5 liter aqueous solution containing 120 g sweetener (stevia) and 2400 ml of flavor (orange) are added to the concentrate. The concentrate is lyophilized. The lyophilizate is milled to the required particle size.

EXAMPLE 2

The description at example 1 is followed except that 600 g sunflower lechitin is given to the cell-free filtered fermentation liquid.

EXAMPLE 3

Antitumor effects of Avé® and the product manufactured according to example 1 (AvéUltra®) in S-180 murine sarcoma tumor model.

In our experiments the antitumor effects of the active ingredients of Avé® (denoted as DEL 59612) and of the product manufactured according to example 1 (AvéUltra®) (denoted as DEL 59615) were investigated in S-180 murine sarcoma tumor model. Antitumor effects of the products were measured by their effects on tumor growth and on overall survival in S-180 sarcoma bearing mice. The experiments were done with equal amounts of the active ingredient.

Inbred SPF (specific pathogen free) female BDF1 mice with 22-24 g body weight were used. Animals were given Altromin feed and tap drinking water ad libitum.

S-180 murine tumor was transplanted (Type: sarcoma. Origin: Chester Beatty Cancer Res. Inst., London, UK. Inoculum: tissue. Mode of transplantation: sub cutaneous (s.c.). Host animal: BDF1 (C57B1 female X DBA/2 male) inbred hybride mouse from SPF hygienic quality certified breed). The transplantation of the tumor was carried out by s.c. transplantation of optimal tumor pieces and/ or fragments into the interscapular region by tweezers. Prior to surgery, animals were narcotized by Nembutal (50 mg/ kg, i.p.).

Animals were treated orally once daily for 10 days (10× qd). For detecting any toxic effect of the treatments, body weights were systematically registered.

Treatments were started after the appearance of the measurable tumor (7 days after tumor transplantation). After randomization groups of 7-7 animals were formed. Randomization was carried out by measuring each animal's tumor volume thus, getting a mean value for tumor size. Mice, having larger or smaller tumor than that of the mean value, were discarded. The average tumor volumes in the groups were equal.

Evaluation of Antitumor Effect:

The antitumor effects of the products were determined by comparing changes of tumor volume and overall survival in the treated and non-treated (control) groups. Digital callipers were used for the continuous measurement of tumour volumes. The determination of tumour volume was done by using the following formula, accepted and used in the literature (Tomayko M. M., Reynolds C. P.: Determination of subcutaneons tumor size in athymic (nude) mice. Cancer Chemother Pharmacol. 24: 148-154, 1989):

$$V = D^2 \times L \times \pi / 6$$

where V=tumour volume, D=shorter diameter, L=longer diameter.

Animals were observed daily, and measurements of tumor volume was done in every second, day.

Results

Effects of DEL samples on the growth of S-180 sarcoma tumor: The results (FIG. 1) of our experiments show that the products denoted as DEL 59615 and DEL 59612 reduced tumor growth by 53% and 20%, respectively.

Effects of DEL samples on overall survival:

The products denoted as DEL 59615 and DEL 59612 lengthened overall survivals of sarcoma mice by 43% and 18%, respectively (FIG. 2).

EXAMPLE 4

Investigation of the effects of the active ingredients of the products Avé® and AvéUltra® in 50H1993 and 111975 human lung cancer cell lines and in SKBR3 human breast cancer cell line. 1050 values are shown in FIG. 3. (The experiments were done with equal amounts of the active ingredient.)

The invention claimed is:

1. A method for the treatment of cancer, which comprises administering to a human an effective amount of a pharmaceutical preparation comprising as an active ingredient
   a high water soluble, amorphous dehydrated product, obtained by fermenting wheat germ in an aqueous medium in the presence of microorganisms of the *Saccharomyces* genus, and
   a) concentrating and cooling the thus resulted fermentation liquid, and adding to the resulted fermentation liquid 0.1-5% (w/w) taste improving material(s) and optionally surfactant(s) and other auxiliary material(s), dissolved in water and lyophilizing the mixture thus obtained, or
   b) cooling the thus resulted fermentation liquid, and adding to the resulted fermentation liquid 0.1-5% (w/w) taste improving material(s) and optionally surfactant(s) and other auxiliary material(s), dissolved in water, and concentrating and lyophilizing the mixture thus obtained,
and optionally pharmaceutical auxiliary materials.

2. The method for the treatment of cancer according to claim 1, wherein the surfactants are surface-stabilizing, dispersing or emulsifying agents.

3. The method for the treatment of cancer according to claim 1, wherein the surfactants are selected from the group consisting of at least one of polyoxyethylene alkyl ethers, polyoxyethylene sorbitane fatty acid esters, polyethylene glycols, sodium dodecyl sulfate, sodium lauryl sulfate, polyvinylpyrrolidone, block copolymers of ethylene oxide and propylene oxide, acrylic acid polymers, phosphatides, phospholipids and chitosan.

4. The method for the treatment of cancer according to claim 3, wherein the phosphatides are lecithin.

5. The method for the treatment of cancer according to claim 1, wherein the taste improving material(s) are selected from at least one of the group consisting of natural sweeteners and artificial sweeteners, and different flavoring compounds.

6. The method for the treatment of cancer according to claim 5, wherein the natural sweeteners and artificial sweeteners are selected from the group consisting of at least one of Stevia and mono ammonium glycyrrhizinate, and wherein the different flavoring compounds are selected from the group consisting of at least one of fruit extracts, menthol, sweet fennel oil, and citric oil.

7. The method for the treatment of cancer according to claim 6, wherein the Stevia is Stevia rebaudiana extracts.

8. The method for the treatment of cancer according to claim 1, wherein the pharmaceutical preparation is formulated as a tablet, coated tablet, extended release tablet, dragée, granule, sachet, capsule, solution, suspension, emulsion, spray, suppository, ointment, patch, or liposome.

9. The method for the treatment of cancer according to claim 1, wherein the microorganisms of the *Saccharomyces* genus are microorganisms from *Saccharomyces cerevisiae*.

10. A method for the treatment of cancer, which comprises administering to a human an effective amount of a pharmaceutical preparation comprising as an active ingredient a high water soluble, amorphous dehydrated product, obtained by fermenting wheat germ in an aqueous medium in the presence of the microorganisms of *Saccharomyces cerevisiae*, and
    a) concentrating and cooling the thus resulted fermentation liquid, and adding to the resulted fermentation liquid 0.1-5% (w/w) Stevia natural sweetener as taste improving material(s) and optionally surfactant(s) and other auxiliary material(s), dissolved in water and lyophilizing the mixture thus obtained, or
    b) cooling the thus resulted fermentation liquid, and adding to the resulted fermentation liquid 0.1-5% (w/w) Stevia natural sweetener as taste improving material(s) and optionally surfactant(s) and other auxiliary material(s), dissolved in water, and concentrating and lyophilizing the mixture thus obtained,
and optionally adding pharmaceutical auxiliary materials.

11. The method for the treatment of cancer according to claim 10, which comprises administering to a human an effective amount of a pharmaceutical preparation containing 99.00-99.6% (w/w) fermented wheat germ freeze dried extract and 0.4-1% (w/w) Stevia natural sweetener as the taste improving material.

* * * * *